United States Patent [19]

Burris

[11] Patent Number: 5,422,043

[45] Date of Patent: Jun. 6, 1995

[54] DIFFUSER AND DIFFUSING METHOD USING DUAL SURFACE TENSIONS

[76] Inventor: William A. Burris, 7 E. Jefferson Cir., Pittsford, N.Y. 14534

[21] Appl. No.: 329,512

[22] Filed: Aug. 23, 1994

Related U.S. Application Data

[63] Continuation of Ser. No. 21,326, Feb. 23, 1993, abandoned, which is a continuation-in-part of Ser. No. 848,835, Mar. 10, 1992, Pat. No. 5,213,773, which is a continuation-in-part of Ser. No. 670,690, Mar. 18, 1991, Pat. No. 5,207,993, which is a continuation-in-part of Ser. No. 575,622, Aug. 31, 1990, Pat. No. 5,082,558.

[51] Int. Cl.$^6$ ............................................. B01F 3/04
[52] U.S. Cl. ................... 261/122.1; 261/122.2
[58] Field of Search ..................... 261/122.1, 122.2

[56] References Cited

U.S. PATENT DOCUMENTS

| | | | |
|---|---|---|---|
| 1,117,601 | 11/1914 | Porter | 261/122.1 |
| 2,774,585 | 12/1956 | Wirts | 261/122.1 |
| 3,315,895 | 4/1967 | Klingbeil et al. | 261/122.1 |
| 3,520,416 | 7/1970 | Keedwell | 261/122.1 |
| 3,644,231 | 2/1972 | Maruya et al. | 261/122.1 |
| 3,978,176 | 8/1976 | Voegeli | 261/122.1 |
| 4,082,893 | 4/1978 | Okita | 428/376 |
| 4,098,964 | 7/1978 | Reber | 429/86 |
| 4,118,447 | 10/1978 | Richter | 261/122.1 |
| 4,288,395 | 9/1981 | Ewing et al. | 261/122.1 |
| 4,445,893 | 5/1984 | Bodicky | 604/165 |
| 4,703,761 | 11/1987 | Rathbone et al. | 128/763 |
| 4,776,343 | 10/1988 | Hubbard et al. | 128/675 |
| 4,849,139 | 7/1989 | Jager | 261/122.2 |
| 4,851,163 | 7/1989 | Stanton et al. | 261/122.1 |
| 5,215,686 | 6/1993 | Sheckler et al. | 261/122.1 |
| 5,262,096 | 11/1993 | Egashira | 26/122.1 |

FOREIGN PATENT DOCUMENTS 712325  7/1954  United Kingdom ............ 261/122.1

OTHER PUBLICATIONS

"Aerosol frother addition in column flotation", by I. M. Flint, P. MacPhail, and G. S. Dobby, The Metalurgical Society of CIM, vol. 81, No. 913, pp. 81–82.

"Relation of the Equilibrium Contact Angle to Liquid and Solid Constitution", by W. A. Zisman, Advances in Chemistry Series, pp. 1–3, 16–17, 30–31, 46–47.

"Size Reduction of Bubbles by Orifice Mixer", by H. Unno and I. Inoue, Tokyo Institute of Technology, Graduate School at Nagatsuta, Yokohama 227, Japan, 1979, pp. 1571, 1576, 1578.

*Primary Examiner*—Tim Miles
*Attorney, Agent, or Firm*—Eugene Stephens & Associates

[57] ABSTRACT

A diffuser for dispersing gas bubbles into a liquid is formed of gas permeable material having a high surface tension at an interface with the liquid and a low surface tension in a region inward from the interface. The upstream region with the low surface tension resists liquid backflow, and the high surface tension of the interface keeps the bubbles small as they depart from the diffuser and enter the liquid.

30 Claims, 1 Drawing Sheet

DIFFUSER AND DIFFUSING METHOD USING DUAL SURFACE TENSIONS

RELATED APPLICATIONS

This is a continuation of parent application Ser. No. 08/021,326, filed Feb. 23, 1993, entitled DIFFUSER AND DIFFUSING METHOD USING DUAL SURFACE TENSIONS, now abandoned, which in turn is a continuation-in-part of application Ser. No. 848,835, filed Mar. 10, 1992, entitled TREATMENT OF LIQUID ON DEMAND, and issued on May 25, 1993 as U.S. Pat. No. 5,213,773, which in turn is a continuation-in-part of application Ser. No. 670,690, filed Mar. 18, 1991, entitled BATCH LIQUID PURIFIER, and issued on May 4, 1993 as U.S. Pat. No. 5,207,993, which in turn is a continuation-in-part of application Ser. No. 575,622, filed Aug. 31, 1990, entitled CONTACT LENS PURIFICATION SYSTEM, and issued on Jan. 21, 1992 as U.S. Pat. No. 5,082,558.

TECHNICAL FIELD

This invention involves diffusers arranged for dispersing gas bubbles into a liquid.

BACKGROUND

Many processes require that a gas be bubbled into a liquid via a diffuser, and many forms of diffusers exist for this purpose. In general, smaller gas bubbles from the diffuser speed up the dissolving of the gas into a liquid, but a diffuser that forms smaller gas bubbles generally offers greater resistance to the gas flow and thus requires more energy. I prefer a diffuser that consumes as little energy as possible so that a low pressure is adequate to force the gas through the diffuser and disperse it into the liquid as fine bubbles. I also prefer that a fine bubble diffuser stay clean and unclogged, even if operated intermittently.

Commercially available diffusers generally do not meet these requirements. Ceramic diffusers, for example, can make fine bubbles but require a substantial gas pressure to do this. Also, if such diffusers are operated intermittently, as required for some processes, then liquid can enter and clog pores of the diffuser. Once liquid has seeped into the diffuser pores, forcing gas back through the diffuser to reestablish bubbling requires even more pressure, because driving liquid rather than gas through the diffuser pores takes more energy. Liquids seeping into diffuser pores can also carry contaminates such as particles or dissolved solids into the pores where they clog the diffuser.

In an effort to make a more efficient diffuser that consumes less energy and produces very fine bubbles, I investigated many possible materials. This led to a discovery of materials and requirements that perform very well as a diffuser, keeping the bubbles fine, consuming little energy, and keeping pores substantially clear of liquid or clogging material. The diffusers I prefer also resist liquid backflow so that a separate valve for this purpose is not required.

SUMMARY OF THE INVENTION

I have found that forming a diffuser of gas permeable material with two different surface energies can improve diffuser performance. The diffuser surface in contact with the liquid into which bubbles are dispersed has a high surface energy that keeps the bubbles fine. As bubbles form around diffuser pores open at the liquid interface surface, they depart from the diffuser surface and enter the liquid at a smaller size, if the diffuser material has a high surface energy at the liquid interface. In diffuser regions spaced inward from the liquid interface surface, the porous or permeable diffuser material has a lower surface energy that would not produce fine bubbles. The lower surface energy of the inner diffuser material can be a characteristic of a material that offers a high resistance to liquid backflow so that a separate check valve against liquid backflow is not required. The liquid flow resistant materials with the lower surface energies not only block liquid backflow, but resist liquid transport of dissolved or particulate solids that would clog the diffuser. Preventing liquid backflow also reduces the need for displacing liquid from diffuser pores on start-up.

The two surface energies or tensions used in my diffuser can be achieved in several ways including: two different diffuser materials arranged next to each other, a single diffuser material having a coating or treatment on its liquid interface surface, and a single material that can develop a high surface tension on its exterior liquid interface surface while maintaining a low surface tension within a porous interior. An example of the latter would be a micro porous diffuser material with a low surface tension when dry, but having an ability to adsorb water on its liquid contacting surface so that the adsorbed water increases the surface energy of the diffuser interface surface.

Combining the different surface energies of gas permeable materials into a diffuser that is made thin, and especially has a thin interface layer, can reduce the pressure drop experienced in forcing gas through the diffuser. Keeping a low diffuser pressure drop while also resisting liquid backflow further improves efficiency over prior diffusers requiring separate liquid backflow valves that add to the total gas pressure drop. Keeping the gas pressure drop low reduces the diffuser energy consumption and improves the efficiency of the gas bubbling process. Making the diffuser of one or two thin layers of flexible material having the required high and low surface energies can help make the diffuser self-cleaning so that its pores do not tend to clog during idle periods.

DRAWINGS

FIG. 1 schematically represents a dual surface tension diffuser according to my invention, with the diffuser layers enlarged for purposes of illustration.

FIG. 2 is an enlarged, schematic view of another preferred embodiment of a diffuser according to my invention.

DETAILED DESCRIPTION

Figure 1:
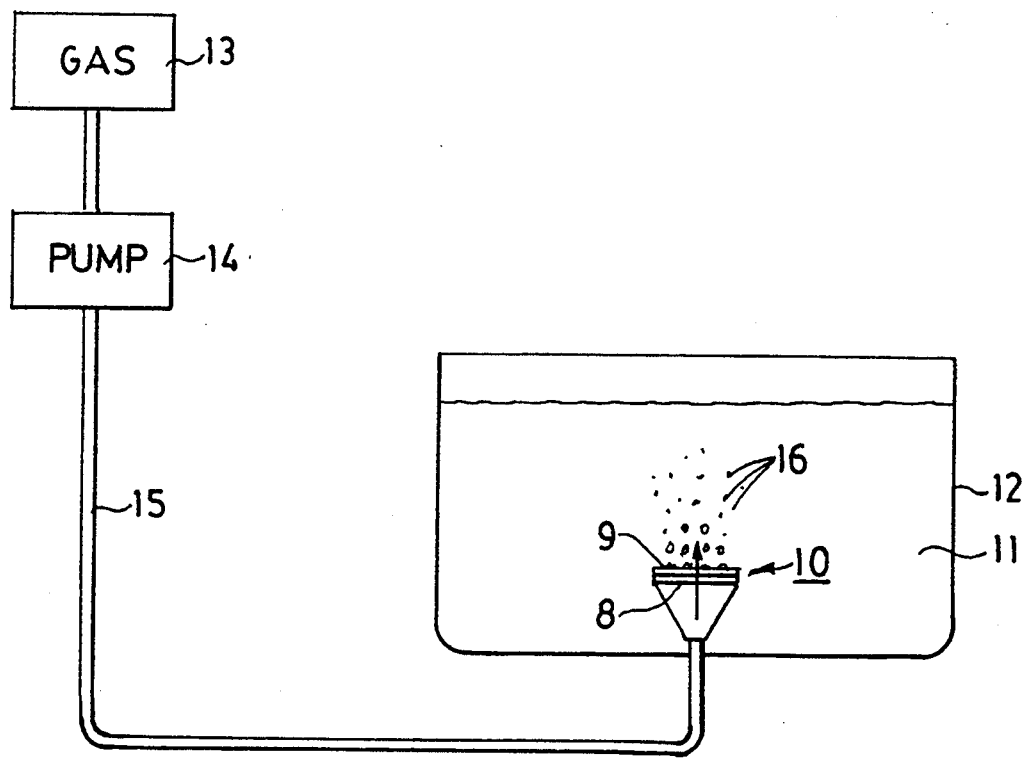

Diffusers are used in a multitude of processes involving many different liquids into which many different gases and mixtures of gases are bubbled. What all these have in common is illustrated schematically in FIG. 1 showing a diffuser 10 arranged beneath the surface of a liquid 11 in a container 12 so that gas from a supply 13 can be delivered by a pump 14 through a line 15 to be dispersed as fine bubbles 16 delivered via diffuser 10 into liquid 11.

Diffuser 10 is formed of an outer, downstream, or liquid interface layer 9 having a high surface tension and an inner or upstream layer 8 having a low surface tension. Both layers 8 and 9 are permeable to gas flow in a direction indicated by an arrow, and at least layer 9 is porous. Layers 8 and 9 are preferably arranged adjacent each other and can be bonded to each other. For illustration purposes, layers 8 and 9 are somewhat enlarged in the drawings.

Layers 8 and 9 need not be formed of separate and distinct materials, as explained more fully below, providing that they differ in effective surface tension, or surface energy, which is an equivalent expression. The dividing point between the surface energies of layers 8 and 9 is preferably about 46 dynes/centimeter, with layer 9 having a surface energy higher than 46 dynes/centimeter and layer 8 having a surface energy lower than 46 dynes/centimeter. The difference in surface energy between layers 8 and 9 does not have to center around this number, though; and since other variables affect diffuser performance, these can also affect the difference in the number values of the surface energies of layers 8 and 9.

The higher surface tension of layer 9 makes it more wettable or hydrophilic and keeps the bubble size small. As gas bubbles form around the pores in layer 9, they can depart from layer 9 and enter liquid 11 at a smaller size than if the bubbles were to enter liquid 11 directly from layer 8, which is less wettable and more hydrophobic. Bubbles entering liquid 11 directly from layer 8 would agglomerate into larger sizes before departing from layer 8, but the higher surface energy of layer 9 more readily releases bubbles from its liquid interface surface so that the bubbles are kept small as they depart from layer 9 and enter liquid 11, resulting in finer bubbles that are more readily dissolved in liquid 11.

Commercially available diffusers can make bubbles in the 2-3 millimeter size range and larger. Dual surface energy diffuser 10 can substantially improve on this, with bubbles in sizes of less than 2 millimeters: bubble sizes no larger than 1.5 millimeters, for example, are readily attainable; and even sizes smaller than 1 millimeter can be made. Although bubble size is one important factor in the performance of a diffuser, energy consumption, self-cleaning ability, and resistance to liquid backflow are also important, as explained more fully below.

Layer 8, with its lower surface energy, resists backflow of liquid 11 against the direction of gas flow. Keeping liquid 11 from flowing through layer 8 helps solve several problems: it helps keep the pores in layer 8 clean; it reduces the need for forcing liquid out of pores in layer 8 when pump 14 starts up; and it reduces the need for any separate valve blocking liquid backflow.

One way that layer 8 can provide the desired resistance to liquid backflow is by being formed of a porous material with tiny pores and a low surface energy. Generally, the resistance of a porous layer 8 to liquid backflow can be increased by reducing its pore sizes and lowering its surface energy. The amount of liquid backflow resistance required should be adequate to resist the pressure caused by the liquid height above layer 8 tending to force liquid into layer 8 when gas is not flowing through layer 8. Materials such as porous polytetrafluoroethylene have been developed with tiny pore sizes and low surface energy so that they resist liquid penetration, while allowing gas to pass through. Other gas permeable and liquid flow resistant materials can also be made from other micro porous materials such as halogenated organic polymers, silicone polymers, and hydrocarbon polymers such as polyethylene and polypropylene. The surface tension of porous materials can also be lowered by various treatments to increase liquid flow resistance. Such treatments include application of low surface tension liquids or solutions or suspensions of low surface tension compounds such as hydrocarbons, hydrogenated organic compounds, silanes, and silicones. Such liquid flow resistant materials are preferred for layer 8; but if they were used without layer 9, they would make very poor diffusers because of the large bubble sizes they would produce.

Another way that low surface energy layer 8 can be made gas permeable and resistant to liquid backflow is by forming layer 8 of a perforated elastomer, such as a natural or synthetic rubber, or rubber-like material. A perforated elastomeric layer 8 is given some freedom of flexible movement, as shown schematically in FIG. 2, so that layer 8 can flex in response to gas flow, which allows perforations to open enough to permit gas throughflow. When gas flow stops, layer 8 elastically returns to its original flat position, which closes its perforations and prevents liquid backflow. A porous layer 9 is arranged adjacent layer 8 and is also made of flexible material to accommodate the elastic movement of layer 8. Porous layer 9 at the liquid interface then keeps bubbles finer than if bubbles were dispersed into liquid directly from layer 8.

The total thickness of layer 8 is a factor in its resistance to gas flow. Generally, making layer 8 thinner allows gas to flow more readily through layer 8 and helps diffuser 10 consume less energy. The layer 8 resistance to liquid backflow is preferably sufficient so that layer 8 can be made as thin as a film or fabric, for example, and still not allow liquid 11 to flow through the thickness of layer 8. Although fine pores or perforations in layer 8 offer some resistance to gas flow, layer 8 contributes to diffuser efficiency by reducing the need for a separate valve blocking liquid backflow.

I prefer that the total pressure drop through diffuser 10 be 4 psi or less per unit of diffuser area at a moderate gas flow rate producing fine bubbles. This is significantly less than the pressure drop caused by commercially available diffusers able to produce the same size bubbles at the same rate. A low pressure drop means low energy consumption and a more efficient diffuser, and some diffusers made according to my invention have required pressure drops of as low as 2 psi, and even 1 psi, to produce a moderate flow of bubbles smaller than 1 millimeter.

Layer 9 is also preferably made thin so that it too provides little resistance to gas flow and assures that diffuser 10 consumes little energy. Another important reason for keeping layer 9 thin is its higher surface energy which permits liquid 11 to penetrate it more readily. Keeping layer 9 as thin as possible correspondingly limits the depth of penetration of liquid and clogging materials carried by the liquid, to minimize pore clogging when pump 14 is off and to minimize the need to force liquid out of pores when pump 14 starts up.

One preferred way to give layers 8 and 9 the necessary thinness and dual surface tension requirements is to use a porous material with a low surface energy that increases when the material surface adsorbs liquid. An example of this is spun-bonded fabrics or webs of polyethylene and polypropylene, which have low surface energies that increase when their porous surfaces adsorb water. To take advantage of this requires that liquid 11 include water, which is the case for many processes. It also requires that the material pores be very small, such as 1 micron or less. The water adsorption on the large surface area provided by the tiny pores raises the surface tension, which can produce fine bubbles, if the surface tension of the porous material is not too low when dry. Once the porous interface surface has adsorbed water and thus increased its surface energy, it forms high surface tension layer 9 at the interface with liquid 11 while maintaining a low surface energy throughout its unwetted interior forming gas side layer 8.

Another way of forming layers 8 and 9 is to use two different porous materials, which can differ from each other, not only in their chemical nature, but in their structural and porous nature: they can be porous solids; bonded fibers; sintered particles; and flocked, felted, or woven fabric. The materials can be both natural and synthetic and are preferably organic or silicone polymers. For interface layer 9, they can also include inorganic materials such as fabrics made of glass, quartz, and ceramics.

The pore sizes of the layer 9 material can be larger than the pore sizes of the layer 8 material, which may be smaller to resist liquid penetration. Small pore sizes contribute to small bubble sizes if layers 8 and 9 are integral or are bonded together, and uniformity of pore sizes in layer 9 is advantageous for ensuring that the gas flow does not concentrate through larger pores. The higher surface energy of layer 9 cooperates with preferably uniform pore sizes to keep the bubble sizes small, even though the bubbles may become larger than the material pores before they depart from the liquid interface surface.

Figure 2:
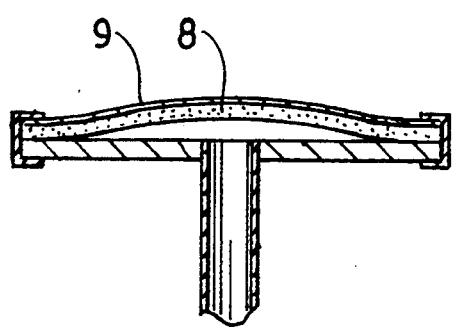

One material I prefer for layer 9 is acetate rayon fabric. A woven fabric for layer 9 has the advantage of uniform pore sizes in a thin material; and fabrics are also flexible, which makes it easier to dislodge dirt from their pores. Fabrics of other types of rayon, cotton, linen, and silk have similar advantages, but the natural fiber materials are more subject to attack by microorganisms and chemicals. A material selected for any specific process must be resistant to the gas and liquids involved, of course. Nonwoven fabrics such as spunbonded fabrics are also preferred materials for layer 9, especially if their pore sizes are made uniform. Fabrics of inorganic fibers of glass, quartz, and ceramics, woven or bonded in a fine and uniform porous configuration, are also suitable for layer 9. Among all the choices of materials for layer 9, those that are flexible are preferred for use in combination with a flexible layer 8, and especially for a perforated elastomeric layer 8, such as shown in FIG. 2.

Porous materials suitable for use in layer 9 generally have a higher surface energy of more than 46 dynes/centimeter. A likely characteristic of suitable materials is having hydrophilic groups such as hydroxy groups on their polymer chains. Suitable polymers need not necessarily have hydroxy groups to have a sufficiently high surface energy; because amino, quaternary, carboxyl, nitro sulfonic, sulfhydryl, and salts such as sodium carboxylate and sodium sulfonate may also satisfy the high surface energy requirement.

Another possibility for forming diffuser layers 8 and 9 is to form layer 9 as a surface coating or treatment applied to layer 8. Generally, this involves a coating or treatment that produces a high surface energy layer 9 on the liquid interface surface of inner layer 8, to keep bubble sizes small, while inner layer 8 provides liquid backflow resistance. Many surface treatment materials are known to increase surface energy.

I claim:
1. A diffuser for dispersing gas bubbles into a liquid, said diffuser comprising:
 a. a gas permeable upstream layer arranged to afford low pressure resistance to throughflow of gas toward said liquid;
 b. the upstream layer being formed of a low surface tension material with fine enough pores to have a high resistance to backflow of said liquid.
 c. a thin, gas permeable interface layer disposed downstream of said upstream layer between said upstream layer and said liquid, said interface layer also being arranged to afford low pressure resistance to throughflow of gas toward said liquid;
 d. said interface layer being formed of a material having a surface tension substantially higher than the low surface tension material of the upstream layer; and
 e. the surface tension of the interface layer being high enough for keeping the size of the bubbles substantially smaller than the bubbles would be if they formed on and departed from the low surface tension layer.

2. The diffuser of claim 1 wherein said upstream layer is formed of a porous resin and said interface layer is formed of a high surface tension material coated onto an interface surface of said porous resin.

3. The diffuser of claim 1 wherein at least one of said layers is formed of resin.

4. The diffuser of claim 1 wherein at least one of said layers is formed of fibers.

5. The diffuser of claim 1 wherein at least one of said layers is formed of fabric.

6. The diffuser of claim 1 wherein said upstream layer has a surface energy of less than 46 dynes/cm, and said interface layer has a surface energy of more than 46 dynes/cm.

7. The diffuser of claim 1 wherein said upstream layer is a perforated elastomer.

8. A diffuser comprising:
 a. a pair of gas permeable layers juxtaposed to allow gas to flow first through a gas side layer and second through a liquid side layer to be dispersed as bubbles delivered to a liquid from the liquid side layer;
 b. the gas side layer having a high resistance to backflow of said liquid;
 c. the gas side layer having a low surface tension;
 d. the liquid side layer being thin and having a surface tension substantially higher than said low surface tension, for keeping the size of said bubbles substantially smaller than said bubbles would be if they entered said liquid directly from said low surface tension material of the gas side layer; and
 e. said layers being thin enough to afford low pressure resistance to gas flow.

9. The diffuser of claim 8 wherein at least one of said layers is formed of porous resin.

10. The diffuser of claim 8 wherein at least one of said layers is formed of fibers.

11. The diffuser of claim 8 wherein at least one of said layers is formed of fabric.

12. The diffuser of claim 8 wherein the gas side layer is a porous resin and the liquid side layer is a coating applied to an interface surface of the porous resin.

13. The diffuser of claim 8 wherein said gas side layer has a surface energy of less than 46 dynes/cm, and said liquid side layer has a surface energy of more than 46 dynes/cm.

14. The diffuser of claim 8 wherein said gas side layer is a perforated elastomer.

15. A method of diffusing gas bubbles into a liquid, said method comprising:
   a. pumping gas through a permeable material having a low surface tension and a high resistance to liquid flow in a direction counter to the flow of said gas;
   b. dispersing said gas through a layer of porous material disposed adjacent a downstream side of the permeable material, the porous material having a higher surface tension than said low surface tension permeable material so that small bubbles of said gas form on and depart from said higher surface tension material into said liquid; and
   c. making said lower and higher surface tension materials thin enough to form low pressure resistance to gas flow through both materials.

16. The method of claim 15 including making the porous material flexible to reduce clogging of pores from intermittent operation.

17. The method of claim 15 wherein said higher surface tension layer is formed of a porous material arranged in contact with said low surface tension material.

18. The method of claim 15 including forming said higher surface tension layer of fibers.

19. The method of claim 15 including forming said higher surface tension layer of fabric.

20. The method of claim 15 including forming said low surface tension material of a perforated elastomer.

21. The method of claim 15 including selecting said low surface tension material to have a surface energy of less than 46 dynes/cm and selecting said higher surface tension layer to have a surface energy of more than 46 dynes/cm.

22. The method of claim 15 including forming said low surface tension material of porous resin.

23. The method of claim 22 including forming said higher surface tension layer as a coating applied to a liquid-facing surface of said permeable material.

24. A diffuser for dispersing a gas flow into bubbles directed into a liquid, said diffuser comprising:
   a. a gas inflow side of said diffuser being formed of a permeable material having a low surface tension and small pores forming a high resistance to backflow of liquid;
   b. a gas outflow side of said diffuser being formed of a separate porous material disposed adjacent the inflow side material and having a surface tension at least several dynes/cm higher than said low surface tension so that bubbles forming on and departing from said higher surface tension surface of the outflow side material are kept to a small size as they enter said liquid; and
   c. said diffuser being thin enough to afford a low pressure resistance to gas flow through both materials.

25. The diffuser of claim 24 wherein said higher surface tension of said gas outflow side of said diffuser is formed by a coating of the separate porous material on a surface of said low surface tension inflow side material.

26. The diffuser of claim 24 wherein said higher surface tension outflow side of said diffuser is formed of fibrous material.

27. The diffuser of claim 24 wherein said higher surface tension outflow side of said diffuser is formed of fabric material.

28. The diffuser of claim 24 wherein said low surface tension material is a perforated elastomer.

29. The diffuser of claim 24 wherein said low surface tension material has a surface energy of less than 46 dynes/cm, and said higher surface tension material has a surface energy of more than 46 dynes/cm.

30. A diffuser for dispersing a gas flow into bubbles directed into a liquid containing water, said diffuser comprising:
   a. a gas inflow side of said diffuser being formed of a spun-bonded, permeable fabric of resin material having a low surface tension and small pores less than one micron in diameter forming a high resistance to backflow of liquid;
   b. water being adsorbed on a gas outflow side of said permeable fabric material so that the surface tension of the gas outflow side of said permeable fabric material is at least several dynes per centimeter higher than the low surface tension of the gas inflow side of said permeable fabric material so that bubbles forming on and departing from said higher surface tension surface are kept to a small size as they enter said liquid; and
   c. said permeable fabric material being thin enough to afford a low pressure resistance to gas flow through the diffuser.

* * * * *